(12) United States Patent
Wolff et al.

(10) Patent No.: US 12,336,832 B2
(45) Date of Patent: Jun. 24, 2025

(54) P-WAVE DETECTION USING INTRACARDIAC ELECTRODES

(71) Applicant: BIOSENSE WEBSTER (ISRAEL) LTD., Yokneam (IL)

(72) Inventors: Marc Wolff, Leipzig (IL); Elad Nakar, Timrat (IL); Eliyahu Ravuna, Kiryat Ata (IL); Nir Yanovich, Binyamina-Giv'at Ada (IL); Hadar Reuveny, Kibbutz Evron (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 188 days.

(21) Appl. No.: 17/692,232

(22) Filed: Mar. 11, 2022

(65) Prior Publication Data
US 2023/0284960 A1    Sep. 14, 2023

(51) Int. Cl.
*A61B 5/353*    (2021.01)
*A61B 5/00*    (2006.01)
*A61B 5/283*    (2021.01)
*A61B 5/367*    (2021.01)

(52) U.S. Cl.
CPC .............. *A61B 5/353* (2021.01); *A61B 5/283* (2021.01); *A61B 5/367* (2021.01); *A61B 5/7235* (2013.01)

(58) Field of Classification Search
CPC ......... A61B 5/353; A61B 5/283; A61B 5/367; A61B 5/7235
See application file for complete search history.

(56) References Cited

U.S. PATENT DOCUMENTS

| | | | |
|---|---|---|---|
| 5,078,133 A | 1/1992 | Heinz | |
| 6,745,075 B2 | 6/2004 | Björling | |
| 7,123,954 B2 | 10/2006 | Narayan | |
| 7,174,210 B1 | 2/2007 | Levine | |
| 8,989,852 B2 | 3/2015 | Gill | |
| 2004/0133113 A1* | 7/2004 | Krishnan | A61B 5/1076 600/508 |
| 2010/0121394 A1 | 5/2010 | Gill | |
| 2016/0135707 A1 | 5/2016 | Li | |

(Continued)

FOREIGN PATENT DOCUMENTS

EP    2405969 B1    3/2014

OTHER PUBLICATIONS

International Search Report for corresponding PCT Appln. No. PCT/IB2023/051507 dated May 11, 2023.

(Continued)

*Primary Examiner* — Catherine M Voorhees
(74) *Attorney, Agent, or Firm* — Scully, Scott, Murphy & Presser, PC

(57) ABSTRACT

A method includes acquiring intracardiac unipolar signals and intracardiac bipolar signals at a given region of a heart of a patient. The unipolar signals are pruned by eliminating ones of the unipolar signals that correspond in time to respective bipolar signals. One or more unipolar signals are identified among the pruned unipolar signals, that are associated with far-field P-waves. Using the identified P-waves, a window of interest (WOI) is set on electrograms acquired in an atrium of the heart, and, using the electrograms having the set WOI, an electrophysiological (EP) map is generated, of the atrium indicative of atrial tachycardia (AT) tissue locations therein.

11 Claims, 4 Drawing Sheets

(56) References Cited

U.S. PATENT DOCUMENTS

| | | | | |
|---|---|---|---|---|
| 2020/0281494 | A1* | 9/2020 | Eliyahu | A61B 5/742 |
| 2021/0386355 | A1* | 12/2021 | Ravuna | A61B 5/7267 |
| 2022/0051091 | A1* | 2/2022 | Ravuna | A61B 5/7267 |
| 2022/0181025 | A1* | 6/2022 | Palti | A61B 5/7264 |
| 2022/0400951 | A1* | 12/2022 | Haeusser | A61B 5/341 |

OTHER PUBLICATIONS

Mechulan Alexis et al: "An improved window of interest for electroanatomical mapping of atrial tachycardia", Journal of Interventional Cardiac Electrophysiology, Springer New York LLC, US, vol. 63, No. 1, Jan. 27, 2021 (Jan. 27, 2021), pp. 29-37.

Chadi Dib et al: "Successful use of cryo-mapping to avoid phrenic nerve damage during ostial superior vena caval ablation despite nerve proximity", Journal of Interventional Cardiac Electrophysiology, Kluwer Academic Publishers, BO, vol. 22, No. 1, Mar. 7, 2008 (Mar. 7, 2008), pp. 23-30.

* cited by examiner

P-WAVE DETECTION USING INTRACARDIAC ELECTRODES

FIELD OF THE DISCLOSURE

The present disclosure relates generally to electrophysiological (EP) mapping, and particularly to cardiac EP mapping.

BACKGROUND OF THE DISCLOSURE

Methods to detect specific cardiac activations were previously proposed in the patent literature. For example, U.S. Pat. No. 7,174,210 describes how relative refractory windows are opened within both the atrial and ventricular refractory periods for the purposes of determining the atrial rate. In this manner, T-waves occurring during the relative refractory windows are excluded from the atrial rate calculation, whereas any P-waves occurring during the relative refractory windows are counted, thereby achieving a more accurate atrial rate calculation, particularly at high atrial rates.

As another example, U.S. Pat. No. 5,078,133 describes how electrical cardiogenic heart depolarization is detected on a multipolar single probe with the aid of individual electrodes. Bipolar electrodes in the atrium allows for detection of the intra-atrial actions (P-wave) as a first rate control signal for controlling a pacemaker. A second rate control signal other than the P-wave correlating with patient activity is determined in parallel with the P-wave control signal. The two control signals are compared to decide if the intra atrial actions (P-waves) are appropriate control signals. Pace rate control is switched between the two signals in order to produce the most beneficial pacing mode to the patient. This control system can respond to unreliability or instabilities of the intrinsic atrial P-wave signal, for example, fibrillation and shift control to another appropriate rate responsive mode.

The present disclosure will be more fully understood from the following detailed description of the examples thereof, taken together with the drawings in which:

BRIEF DESCRIPTION OF THE DRAWINGS

The present disclosure will be more fully understood from the following detailed description of the examples thereof, taken together with the drawings in which.

DETAILED DESCRIPTION OF EXAMPLES

Overview

Figure 1:
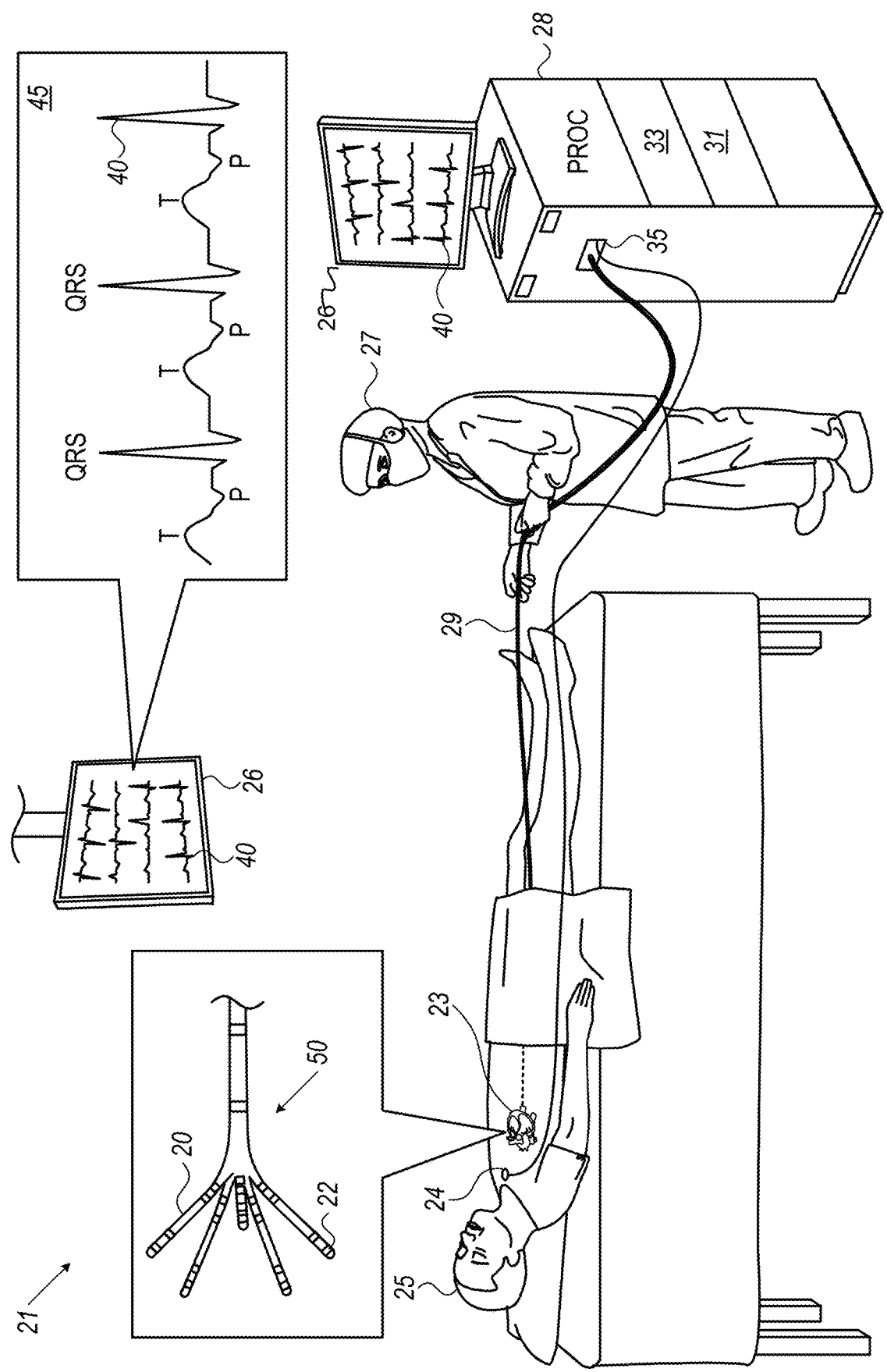
FIG. 1 is a schematic, pictorial illustration of a system for electrophysiological (EP) mapping, in accordance with an example of the present disclosure.

Atrial tachycardia (AT) is a cardiac arrhythmia that occurs when heart tissue is triggered by a source other than the normally functioning sinoatrial node. One possible way to electro-physiologically (EP) map AT using a mapping catheter relies on a physician identifying the P-wave in electrocardiograms (ECGs) acquired by body surface (BS) electrodes, and correctly setting a related window of interest (WOI) for the map. Using the EP map to identify AT arrhythmogenic tissue regions, a physician may ablate atrial tissue to block the AT from occurring.

However, locating a P-wave in BS signals is difficult and at times impossible, because, for example, the P-wave has a low signal-to-noise ratio, a high interpatient variability, and may be missing, or even hidden, within the QRS complex or the T-wave. The difficulty in locating a P-wave increases the chances of an incorrect WOI that leads to an incorrect EP map.

Moreover, other problems in the identification of P-waves are common, such as the presence of complex fractionated EP signals that precede the P-wave. These signals are thought to be critically relevant to the AT mechanism because they are observed to be located at an "exit area" from an isthmus of scarred tissue that is most likely driving the tachycardia. Correctly identifying the isthmus (e.g., on an EP map) is useful because the physician may ablate it to stop the tachycardia.

Examples of the present disclosure that are described hereinafter provide methods and systems to correctly identify and annotate a P-wave during EP mapping. Rather than using BS signals, the disclosed technique uses intracardiac signals. In some examples, the intracardiac signals may be acquired using the mapping catheter itself that is initially deflected, during the EP mapping, toward the inferior vena cava (IVC) or the superior vena cava (SVC), to acquire therein the far-field P-wave unipolar signal and easily eliminate local signals obscuring P wave far field activation because these areas usually do not have any local activity.

In one example, unipolar and bipolar signals are acquired from intracardiac electrodes of the catheter, and a processor analyzes the signals (also called "electrograms," or EGMs) to identify far-field P-waves. The acquisition at the IVC or SVC minimizes the presence of obstructing local activations (detected as bipolar signals), as the IVC and SVC tissues are less active electro-physiologically. Alternatively, the catheter may acquire far-field signals and eliminate local signals by being located in a blood pool of the RA or LA (e.g., rather than in contact with SVC/IVC tissue).

To detect a far-field unipolar signal associated with a far-field P-wave, the processor removes the dominant far-field QRS complex signal from the acquired waveform. The remaining unipolar signal is further analyzed by the processor to detect unipolar activations (corresponding to the P-wave), for example by finding the point in time when the negative unipolar voltage derivative is above a predetermined threshold.

After that, the remaining bipolar signals are further analyzed to find bipolar activations. During time occurrences when unipolar and bipolar activations correspond to each other; namely, in the case of sensing near field activity, the disclosed method assumes that the activations are not due to a P-wave, but rather caused by near-field activations. Thus, in a further analysis of the remaining unipolar signals, unipolar activations that correspond in time to respective bipolar activations are eliminated (e.g., pruned).

The remaining unipolar activations are assumed to be P-waves. The processor identifies, among the pruned unipolar signals, one or more unipolar signals that are associated with far-field P-waves. To this end, further corroboration is typically provided by considering corresponding signals from other electrodes, and/or considering signals from the last N heartbeats, and select those that are stable over time duration comparable to the cycle length of the tachycardia. The different signals are weighted so as to estimate the P-wave activations with higher consistencies. Examples of weights include giving a higher weight to signals from electrodes that do not touch cardiac tissue (e.g., in a blood pool). Alternatively, a weight can be assigned to the votes according to their timing relative to the QRS peak, with weight growing in the vicinity of the QRS peak.

Typically, the processor is programmed in software containing a particular algorithm that enables the processor to conduct each of the processor-related steps and functions outlined above.

System Description

FIG. 1 is a schematic, pictorial illustration of a system 21 for electrophysiological (EP) mapping, in accordance with an example of the present disclosure.

FIG. 1 depicts a physician 27 using an EP mapping Pentaray® catheter 29 to perform an EP mapping of a cardiac chamber (e.g., a right atrium (RA) and/or a left atrium (LA)) of a heart 23 of a patient 25. In should be noted that other catheters may be utilized.

Catheter 29 comprises, at its distal end, an electrode array 50 comprising one or more arms 20, with mapping-electrodes 22 disposed along each of the arms. During the EP mapping procedure, electrodes 22 acquire and/or inject signals from and/or to the tissue of heart 23. In particular, electrodes 22 acquire intracardiac signals, such as atrial electrograms.

The respective locations of mapping-electrodes 22 inside heart 23 (i.e., where the electrograms are measured) are tracked as well, so that a processor 28 may link each acquired IEGM with the location at which the signal was acquired. System 21 externally senses electrical position signals and EP data, such as electrocardiograms (ECG), using a plurality of external electrodes 24 coupled to the body surface of patient 25; for simplicity, three external electrodes 24 may be coupled to the patient's chest, and another three external electrodes may be coupled to the patient's back. For ease of illustration, only one external electrode is shown in FIG. 1.

An example of a system capable of using the sensed electrical position signals to track the locations of mapping-electrodes 22 inside heart 23 of the patient is the CARTO® 3 system (produced by Biosense Webster Inc., Irvine, California). The CARTO® 3 system uses a tracking method named Advanced Current Location (ACL), which is described in detail in U.S. Pat. No. 8,456,182, whose disclosure is incorporated herein by reference. According to this method, processor 28 measures the electrical impedance between at least some of mapping electrodes 22 and each of external electrodes 24 and finds location coordinates of the mapping electrodes using these impedances. Alternatively or additionally, system 21 may apply other methods of position sensing that are known in the art, such as magnetic position sensing, in finding these location coordinates.

The intracardiac signals captured by mapping electrodes 22 are conveyed over a wire link (not shown) that runs through catheter 29 to a data acquisition module 33 via an electrical interface 35. Using the sensed positions to establish spatiotemporal correlations between the electrograms, processor 28 of system 21 generates an EP map, such as an LAT map. The processor stores the EP map in a memory 31. In parallel, processor 28 may present electrogram traces 40 on a display 26 of system 20.

In particular, inset 45 shows an electrogram trace 40 characteristic of AT, in which the P-wave is inverted.

During and/or following the procedure, processor 28 may display an EP map on the display 26, which can be a touchscreen to enable physician 27 to mark clinical inputs on the EP map or on electrogram traces 40, (such as activation paths and/or scar regions), as well as to command the detection of P-waves and to set a window of interest (WOI) for an EP map based on the P-wave occurrences, as described below. Alternatively or additionally, physician 27 may mark the clinical inputs using any other suitable input device, e.g., in the form of a mouse or a trackball.

The example illustration shown in FIG. 1 is chosen purely for the sake of conceptual clarity. Other types of multi-electrode sensing geometries, such as of the Lasso® catheter (produced by Biosense Webster), may also be employed. Additionally, contact sensors may be fitted at the distal end of catheter 29 to transmit data indicative of the physical quality of electrode contact with tissue. In one example, measurements of some electrodes 22 may be discarded because their physical contact quality is poor, and the measurements of other electrodes may be regarded as valid because their contact quality is high.

Although examples of the present disclosure are described above for the sake of concreteness and clarity, with specific reference to the elements of system 21, the principles of the present disclosure may similarly be applied in other EP mapping systems with suitable sensing capabilities. All such alternative examples are considered to be within the scope of the present disclosure.

Processor 28 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm that enables processor 28 to perform the steps described in FIG. 3.

P-Wave Detection Using Intracardiac Electrodes

Figure 2:
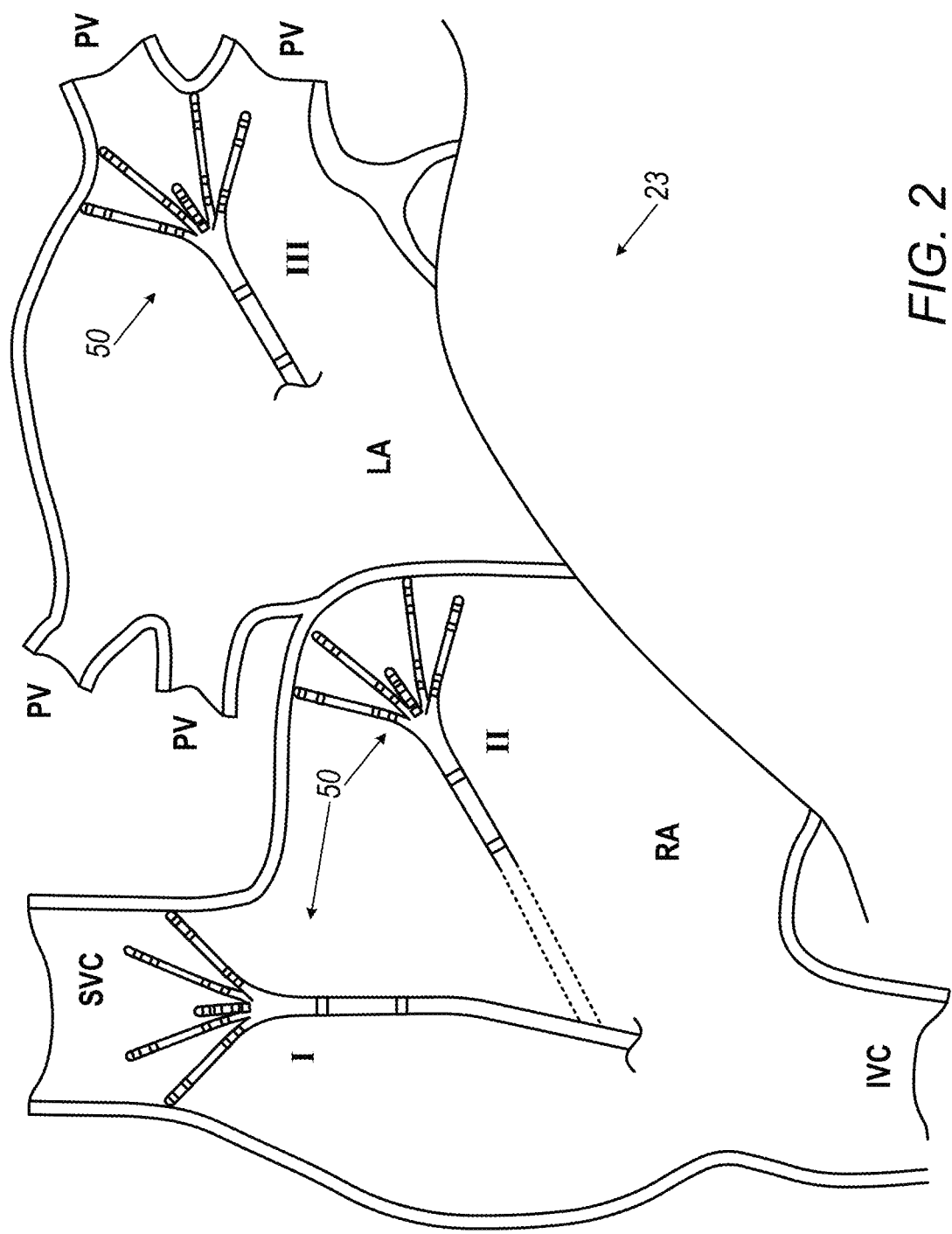
FIG. 2 is a schematic, pictorial illustration of the EP mapping catheter of the system of FIG. 1 in three placements: (I) to enable identification of P waves, P-waves, (II) to EP map the right atrium (RA), and (III) to EP map the left atrium (LA), in accordance with an example of the present disclosure.

FIG. 2 is a schematic, pictorial illustration of the EP mapping catheter of the system of FIG. 1 in three placements within the heart 23: (I) to enable identification of P-waves, (II) to EP map the right atrium (RA), and (III) to EP map the left atrium (LA), in accordance with examples of the present disclosure.

In placement I, electrode array 50 of the catheter is seen in contact with SVC tissue to acquire therein a far-field P-wave signal. This initial step may last several seconds, after which the physician moves the catheter to perform EP mapping of one or two of the atria. FIG. 2 placement II represents an EP mapping session of the RA, whereas placement III represents an EP mapping session of the LA.

The processor analyzes the acquisition at the SVC (or in the IVC, not shown), to set a correct WOI of the electrograms used in generating the EP map, such that aberrant tissue where AT occurs is visible on the EP map. The drawing of FIG. 2 is brought by way of example.

In practice, other catheters may be used for the acquisition of P-waves. The catheter may acquire far-field signals by being located at a blood pool of the RA or LA, rather than in contact with SVC/IVC tissue.

Figure 3:
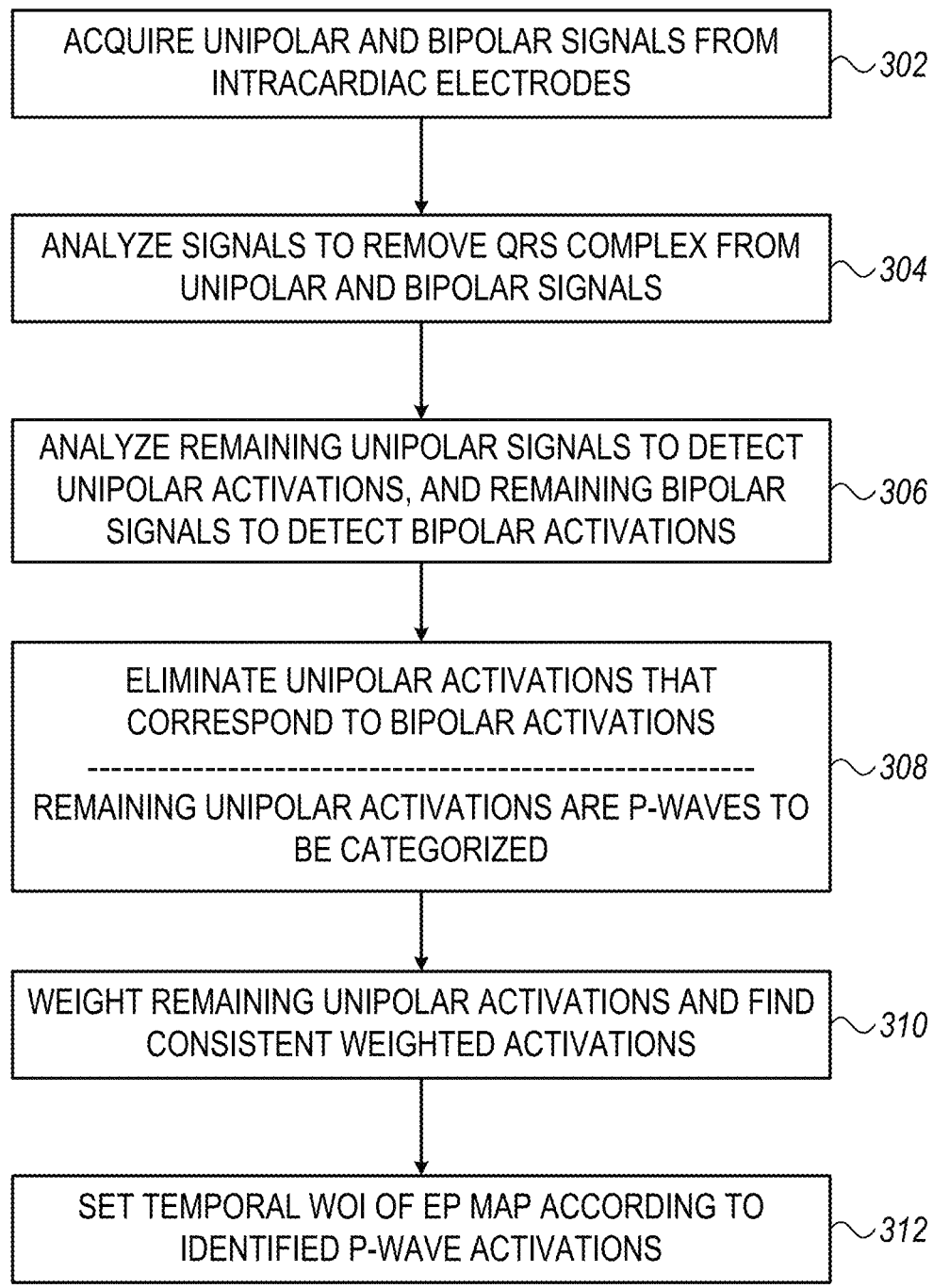
FIG. 3 is a flow chart that schematically illustrates a method for detecting P-waves using intracardiac electrodes and automatically setting a temporal window of interest (WOI) of an EP map, in accordance with an example of the present disclosure.

FIG. 3 is a flow chart that schematically illustrates a method for detecting P-waves using intracardiac electrodes and automatically setting a temporal window of interest (WOI) for EP map, in accordance with an example of the present disclosure. The algorithm, according to the presented example, carries out a process that begins with physician 27 acquiring unipolar and bipolar signals, e.g., from SVC or IVC tissue, using electrode array 50, at signal acquisition step 302. While SVC or IVC tissues are not particularly EP active, some interfering local bipolar signals may still be present there.

Next, at QRS complex removal step 304, processor 28 removes the dominant QRS complex from the unipolar and bipolar signals.

At a next activation detection step 306, processor 28 analyzes the remaining unipolar signals to detect unipolar activations (corresponding to the P-wave), for example, by finding the point in time when the negative voltage derivative is above a predetermined threshold. The threshold can be either a constant or dynamic number. The calculation of the absolute value of the amplitude requires high-pass filtering, for example the signal itself minus the signal after a median filter, or an FIR or IIR filter. The calculation of the negative derivative requires a low-pass filter, such as a Gaussian filter, that does not introduce ripples. The remaining bipolar signals are also similarly analyzed to find intruding bipolar activations. Activations on the bipolar electrogram may be defined as the points in time when the negative derivative and/or the absolute value of the amplitude is above some threshold.

Next, at irrelevant unipolar signal elimination step 308, processor 28 eliminates unipolar signals that correspond (e.g., are coincident with) bipolar signals. Activations that appear on the bipolar electrogram have a high chances of being near-field activations rather than a P-wave.

At P-wave consistency testing step 310, processor 28 considers every activation that appears on the unipolar signal and does not appear on the bipolar signal as a vote, and the processor may calculate majority voting to detect P-waves with high probability. In addition, the last N heartbeats can contribute to voting. Vote consistency can be weighted according to atrial reference cycle length. Specific unipolar deflections are ranked higher if they are consistent with their temporal distance from the atrial reference signal. Every vote can be either 0 or 1, or votes can be real numbers between 0 and 1. For example, the unipolar activation level may contribute to the vote as a positive component to bring it closer to 1, and the strength of the bipolar activation may contribute to the vote as a negative component to bring it closer to 0. The majority voting can then be calculated as the sum of the votes.

Voting may be performed among each of the intracardiac electrodes, including when the electrodes are in a blood pool. In the presence of a "tissue proximity detection" algorithm or a "force measurement" mechanism, electrodes that do not touch the RA or LA cardiac tissue (i.e., are in a blood pool) may have a higher weight in the majority voting algorithm.

Alternatively, a weight can be assigned to the votes according to their timing relative to the QRS peak.

Alternatively, P-waves may be tagged manually on numerous cases during the development. The intracardiac unipolar and bipolar signals and the timing of manually tagged P-waves may be fed to a supervised machine learning algorithm. Using such training, the algorithm will learn to detect segments with a strong enough unipolar activation, without any strong enough bipolar activation. The output of the machine learning algorithm will be the timing of the P-waves.

Finally, at an automatic WOI setting step 312, processor 28 uses the detected (e.g., annotated) P-wave occurrences to correctly set a WOI of the EP map, such as of a local activation time (LAT) map, to visualize tissue locations where AT occurs. The physician may ablate such tissue locations to eliminate the AT.

The above process may be automatic or semi-automatic. For example, to run step 302 and beyond, the physician may click a button of a user interface to command the system to try to detect the P-wave. The processor of the system responds with a progress indicator on display 26 while it processes the signals for several seconds (e.g., up to 10). When calculation ends, the processor lights an indicator of the P wave on the display, such as in an annotation viewer, while the signal continues to be updated in real time.

The flowchart of FIG. 3 is brought by way of example. Additional or alternative algorithmic steps may be included, such as for rejection of interfering far-field signals and noises.

Figure 4:
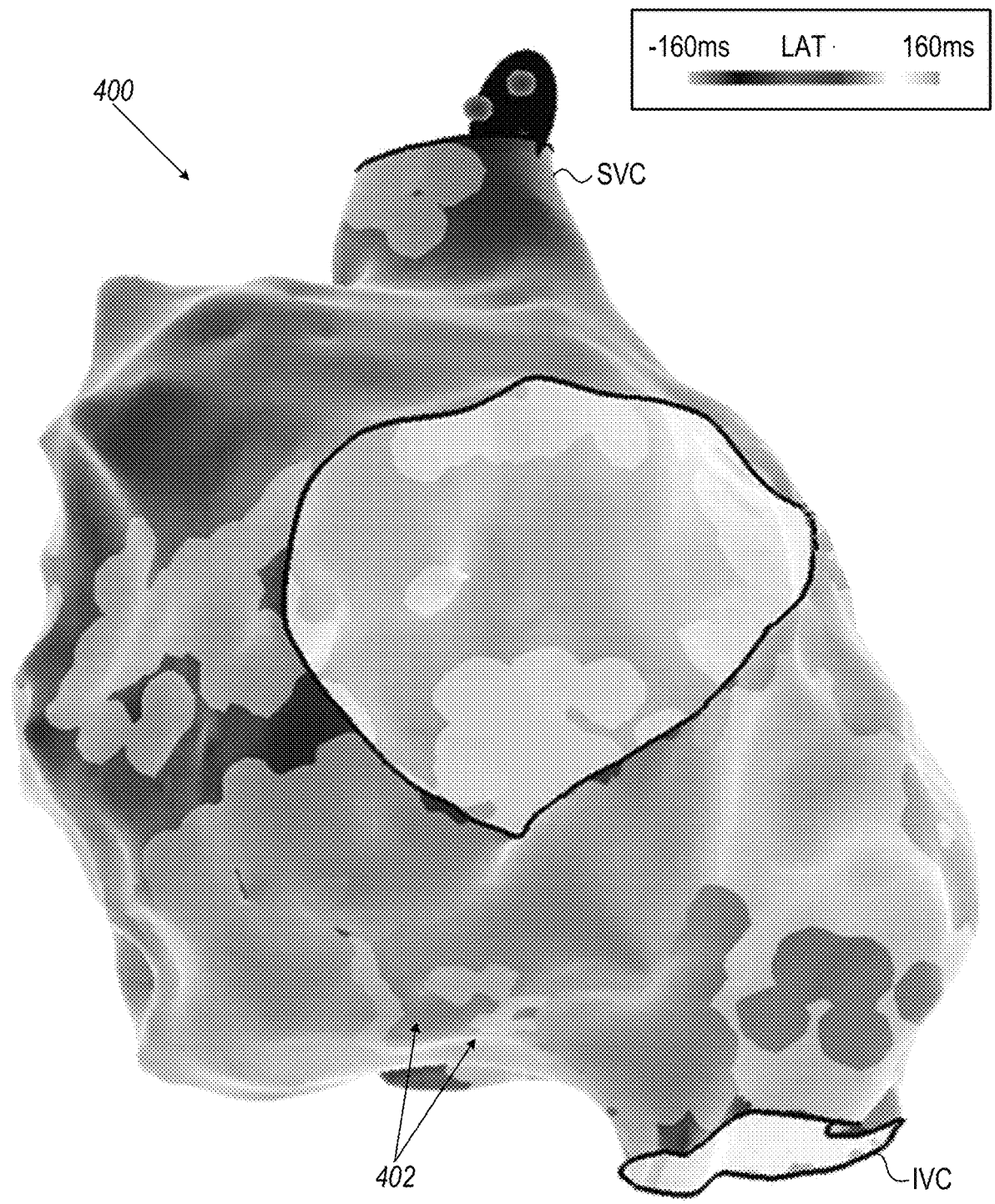
FIG. 4 is a local activation time (LAT) map of a right atrium (RA), that, using the method of FIG. 3, visualizes tissue locations likely causing AT, in accordance with an example of the present disclosure.

FIG. 4 is a local activation time (LAT) map 400 of a right atrium (RA), that, using the method of FIG. 3, visualizes tissue locations 402 likely to be causing AT, in accordance with an example of the present disclosure. LAT map 400 has an asymmetric time scale [−255, 65] mSec, which is the result of the selected WOI being based on the detected P-waves. Using LAT map 400, a physician is able to identify atrial tissue locations 402 that cause AT. Subsequently, the physician may ablate tissue locations 402 to block the AT from occurring.

Example 1

A method includes acquiring intracardiac unipolar signals and intracardiac bipolar signals at a given region of a heart (23) of a patient (25). The unipolar signals are pruned by eliminating ones of the unipolar signals that correspond in time to respective bipolar signals. One or more unipolar signals are identified among the pruned unipolar signals, that are associated with far-field P-waves. Using the identified P-waves, a window of interest (WOI) is on electrograms (40) acquired in an atrium of the heart (23), and, using the electrograms having the set WOI, an electrophysiological (EP) map (400) is generated of the atrium indicative of atrial tachycardia (AT) tissue locations therein.

Example 2

The method according to example 1, wherein the given region is one of a superior vena cava (SVC) and an inferior vena cava (IVC).

Example 3

The method according to example 1, wherein the given region is a blood pool of the atrium.

Example 4

The method according to any of example 1 through 3, wherein identifying the unipolar signals that are associated with the far-field P-waves comprises weighting the unipolar signals based on at least one of (i) a number of electrodes (22) used for acquiring the unipolar signals, (ii) a number of heart cycles over which the unipolar signals have been acquired, and (iii) a timing of occurrence of the unipolar signals relative to a QRS complex.

Example 5

The method according to any of example 1 through 4, wherein setting the WOI comprises adding annotations of the P-waves on the electrograms (40) and using the annotations as a time reference of the WOI.

Example 6

The method according to any of example 1 through 5, wherein acquiring the unipolar signals and the bipolar signals is performed using a catheter (29) fitted with electrodes (22).

Example 7

The method according to any of example 1 through 6, wherein the EP map is a local activation time (LAT) map (400).

Example 8

A method includes acquiring intracardiac unipolar signals and intracardiac bipolar signals at a given region of a heart (23) of a patient (25). A supervised machine learning algorithm is trained to identify P-waves in the acquired unipolar signals by manually tagging the unipolar signals that are indicative of P-waves due to low amplitude of respective bipolar signals. Using the trained machine learning algorithm, one or more unipolar signals are identified among newly acquired unipolar and bipolar signals, that are associated with far-field P-waves. Using the identified P-waves, a window of interest (WOI) is set on electrograms (40) acquired in an atrium of the heart (23), and, using the electrograms (40) having the set WOI, an electrophysiological (EP) map (400) is generated, of the atrium indicative of atrial tachycardia (AT) tissue locations therein.

Example 9

A system includes a memory (31) and a processor (28). The memory (31) configured to store intracardiac unipolar signals and bipolar signals acquired at a given region of a heart (23) of a patient (25). The processor (28) is configured to (i) prune the unipolar signals by eliminating ones of the unipolar signals that correspond in time to respective bipolar signals, (ii) identify, among the pruned unipolar signals, one or more unipolar signals that are associated with far-field P-waves, and (iii) using the identified P-waves, set a window of interest (WOI) on electrograms (40) acquired in an atrium of the heart (23), and generate, using the electrograms (40) having the set WOI, an electrophysiological (EP) map (400) of the atrium indicative of atrial tachycardia (AT) tissue locations therein.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method to identify and annotate a P-wave during EP mapping, comprising:
   acquiring intracardiac unipolar signals and intracardiac bipolar signals at a given region of a heart of a patient, wherein the given region is one of a superior vena cava (SVC) and an inferior vena cava (IVC);
   removing a QRS complex from the unipolar signals and the bipolar signals;
   detecting unipolar activations, of remaining unipolar signals remaining after the QRS complex removal, occurring at first points in time based on a first predetermined electrical activation value threshold;
   detecting bipolar activations, of remaining bipolar signals remaining after the QRS complex removal, occurring at second points in time based on a second predetermined electrical activation value threshold;
   pruning the remaining unipolar signals, by eliminating ones of the remaining unipolar signals that correspond in time to respective bipolar signals;
   identifying, among the pruned unipolar signals, one or more unipolar signals that are associated with far-field P-waves; and
   using the identified far-field P-waves, setting a window of interest (WOI) on electrograms acquired in an atrium of the heart, and generating, using the electrograms having the set WOI, an electrophysiological (EP) map of the atrium indicative of atrial tachycardia (AT) tissue locations therein,
   wherein identifying the one or more unipolar signals that are associated with the far-field P-waves comprises weighting the pruned unipolar signals based on a timing of occurrence of the unipolar signals relative to the QRS complex, and
   wherein setting the WOI comprises adding annotations of the far-field P-waves on the electrograms and using the annotations as a time reference of the WOI.

2. The method according to claim 1, wherein the given region is a blood pool of the atrium.

3. The method according to claim 1, wherein identifying the one or more unipolar signals that are associated with the far-field P-waves comprises further weighting the pruned unipolar signals based on a number of heart cycles over which the unipolar signals have been acquired.

4. The method according to claim 1, wherein acquiring the unipolar signals and the bipolar signals is performed using a catheter fitted with electrodes.

5. The method according to claim 1, wherein the EP map is a local activation time (LAT) map.

6. A system to identify and annotate a P-wave during EP mapping, comprising:
   a memory configured to store intracardiac unipolar signals and bipolar signals acquired at a given region of a heart of a patient, wherein the given region is one of a superior vena cava (SVC) and an inferior vena cava (IVC); and
   a processor, which is configured to:

remove a QRS complex from the unipolar signals and the bipolar signals;

detect unipolar activations, of remaining unipolar signals remaining after the QRS complex removal, occurring at first points in time based on a first predetermined electrical activation value threshold;

detect bipolar activations, of remaining bipolar signals remaining after the QRS complex removal, occurring at second points in time based on a second predetermined electrical activation value threshold;

prune the remaining unipolar signals by eliminating ones of the remaining unipolar signals that correspond in time to respective bipolar signals;

identify, among the pruned unipolar signals, one or more unipolar signals that are associated with far-field P-waves; and use the identified far-field P-waves, set a window of interest (WOI) on electrograms acquired in an atrium of the heart, and generate, using the electrograms having the set WOI, an electrophysiological (EP) map of the atrium indicative of atrial tachycardia (AT) tissue locations therein, wherein the processor is configured to identify the one or more unipolar signals that are associated with the far-field P-waves by weighting the pruned unipolar signals based on a timing of occurrence of the unipolar signals relative to the QRS complex, and wherein setting the WOI comprises adding annotations of the far-field P-waves on the electrograms and using the annotations as a time reference of the WOI.

7. The system according to claim 6, wherein the given region is a blood pool of the atrium.

8. The system according to claim 6, wherein the processor is configured to identify the one or more unipolar signals that are associated with the far-field P-waves by further weighting the pruned unipolar signals based on a number of heart cycles over which the unipolar signals have been acquired.

9. The system according to claim 6, wherein the unipolar signals and the bipolar signals are acquired using a catheter fitted with electrodes.

10. The system according to claim 6, wherein the EP map is a local activation time (LAT) map.

11. The method according to claim 1, further comprising:

detecting the unipolar activations, of the remaining unipolar signals, occurring at the first points in time when a voltage derivative of the remaining unipolar signals is above the first predetermined electrical activation value threshold; and detecting the bipolar activations, of the remaining bipolar signals, occurring at the second points in time when at least one of a voltage derivative of the remaining bipolar signals or an absolute value of a voltage amplitude of the remaining bipolar signals is above the second predetermined electrical activation value threshold.

\* \* \* \* \*